(12) United States Patent
Pietra et al.

(10) Patent No.: US 9,358,228 B2
(45) Date of Patent: *Jun. 7, 2016

(54) THERAPEUTIC COMBINATIONS OF NETUPITANT AND PALONOSETRON

(71) Applicant: Helsinn Healthcare SA, Pazzallo-Lugano (CH)

(72) Inventors: Claudio Pietra, Como (IT); Sergio Cantoreggi, Cagiallo (CH)

(73) Assignee: HELSINN HEALTHCARE SA, Pazzallo-Lugano (CH)

( * ) Notice: Subject to any disclaimer, the term of this patent is extended or adjusted under 35 U.S.C. 154(b) by 226 days.

This patent is subject to a terminal disclaimer.

(21) Appl. No.: 14/351,113

(22) PCT Filed: Oct. 10, 2012

(86) PCT No.: PCT/IB2012/002013
§ 371 (c)(1),
(2) Date: Apr. 10, 2014

(87) PCT Pub. No.: WO2013/057554
PCT Pub. Date: Apr. 25, 2013

(65) Prior Publication Data
US 2014/0256737 A1    Sep. 11, 2014

Related U.S. Application Data

(60) Provisional application No. 61/548,514, filed on Oct. 18, 2011.

(51) Int. Cl.
*A61K 31/473* (2006.01)
*A61K 31/4748* (2006.01)
*A61K 31/496* (2006.01)

(52) U.S. Cl.
CPC .......... *A61K 31/473* (2013.01); *A61K 31/4748* (2013.01); *A61K 31/496* (2013.01)

(58) Field of Classification Search
CPC .................................................... A61K 31/473
USPC ....................................................... 514/253.01
See application file for complete search history.

(56) References Cited

U.S. PATENT DOCUMENTS

| 2006/0223804 A1 | 10/2006 | Shah et al. |
| 2010/0190759 A1 | 7/2010 | Palani et al. |
| 2010/0316678 A1 | 12/2010 | Goodchild |
| 2012/0295879 A1 | 11/2012 | Palani et al. |

FOREIGN PATENT DOCUMENTS

| WO | WO 2006-007540 A1 | 1/2006 |
| WO | WO 2009-000038 A1 | 12/2008 |
| WO | WO 2011-061622 A1 | 5/2011 |

OTHER PUBLICATIONS

Patent Cooperation Treaty Search Report, dated May 16, 2013, which issued during the prosecution of International Patent Application No. PCT/IB2012/002013, which corresponds to the present application.

*Primary Examiner* — Raymond Henley, III
(74) *Attorney, Agent, or Firm* — Clark Sullivan; Troutman Sanders LLP

(57) ABSTRACT

Combinations of netupitant and palonosetron, and methods of using such combinations to treat various pain states and irritable bowel syndrome, are provided.

34 Claims, 15 Drawing Sheets

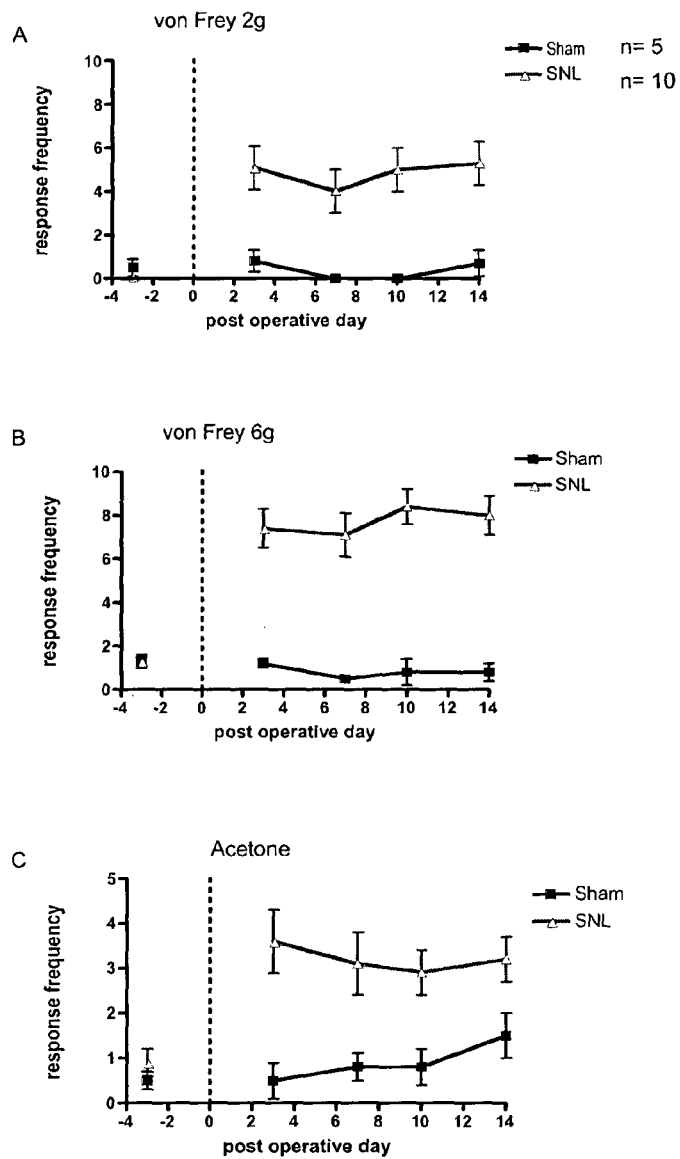
Fig. 1. Temporal development of mechanical and thermal hypersensitivity post nerve injury. Nerve injury induced a significant increase in the number of paw withdrawals to A) vf2g, B) vF 6g and C) acetone stimulation of the ipsilateral hind paw compared with the responses seen in sham controls.

A) Effects of Palonosetron on Ipsilateral Behavioural Responses to vF 2g in SNL ( n= 9) and Sham ( n =5) Animals

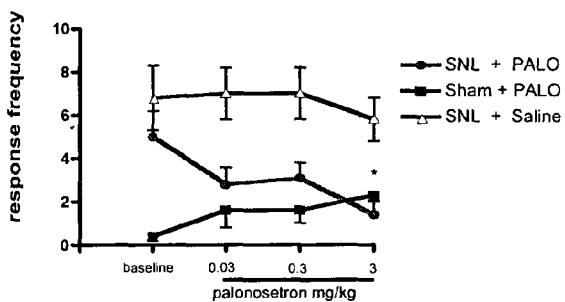

B) Effects of Palonosetron on Ipsilateral Behavioural Responses to vF 6g in SNL ( n= 9) and Sham ( n =5) Animals

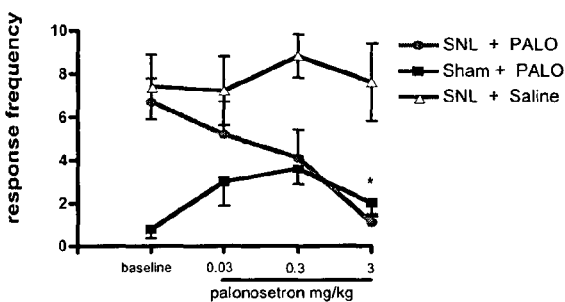

C) Effects of Palonosetron on Ipsilateral Behavioural Responses to Acetone in SNL ( n=9) and Sham ( n=5) Animals

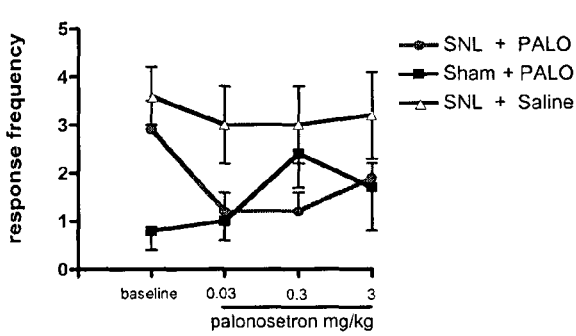

Fig. 2. Effects of palonosetron on the number of paw withdrawals to A) vf2g, B) vF 6g and C) acetone. A dose related reduction in paw withdrawal frequency is seen in the SNL rats only

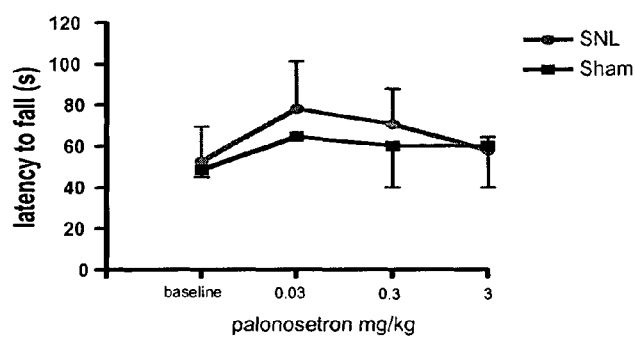
Fig.3 A comparison of total time spent by SNL and Sham rats on a rotarod. Palonosetron (0.03, 0.3 and 3mg/kg) did not impair motor performance in either group. Data presented as mean ± SEM.

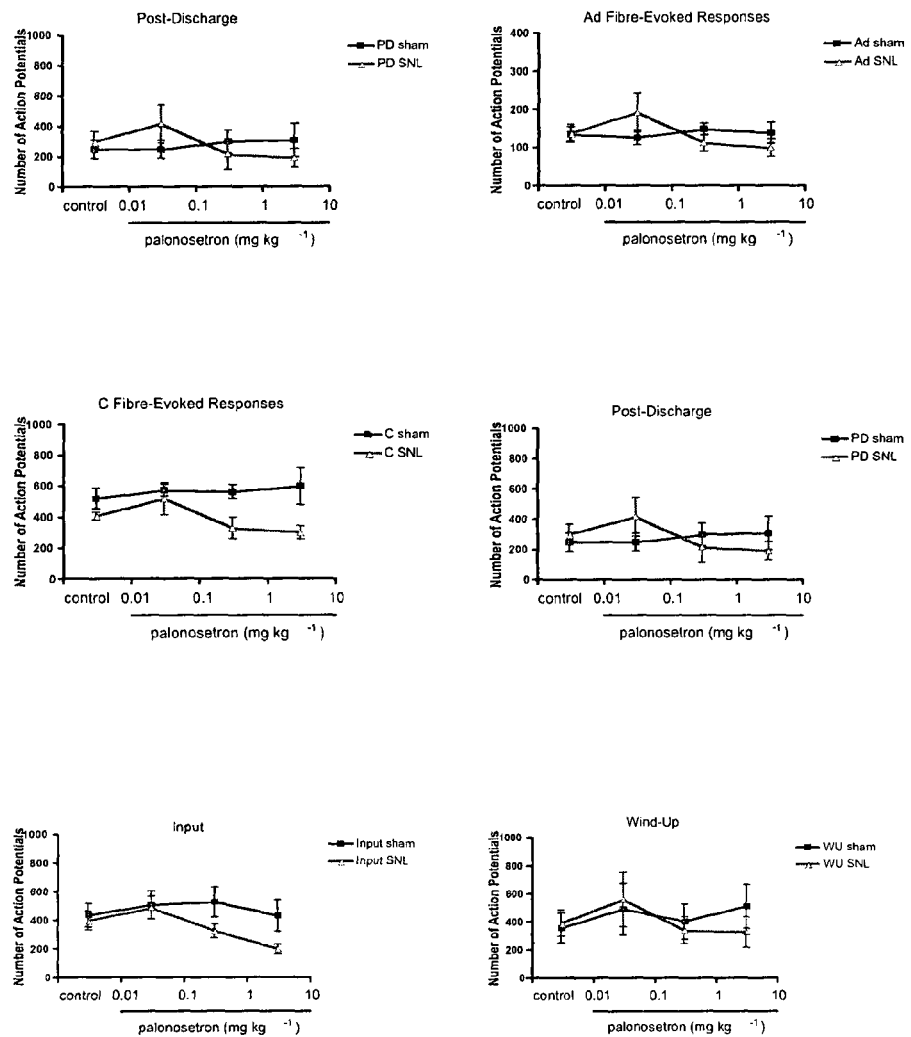
Fig.4. A comparison of the effects of Palonosetron (0.03, 0.3 and 3mg/kg s.c.) on the electrical evoked responses of spinal dorsal horn neurones in sham and SNL. Data are expressed as the mean percentage of pre-drug control values ± S.E.M.

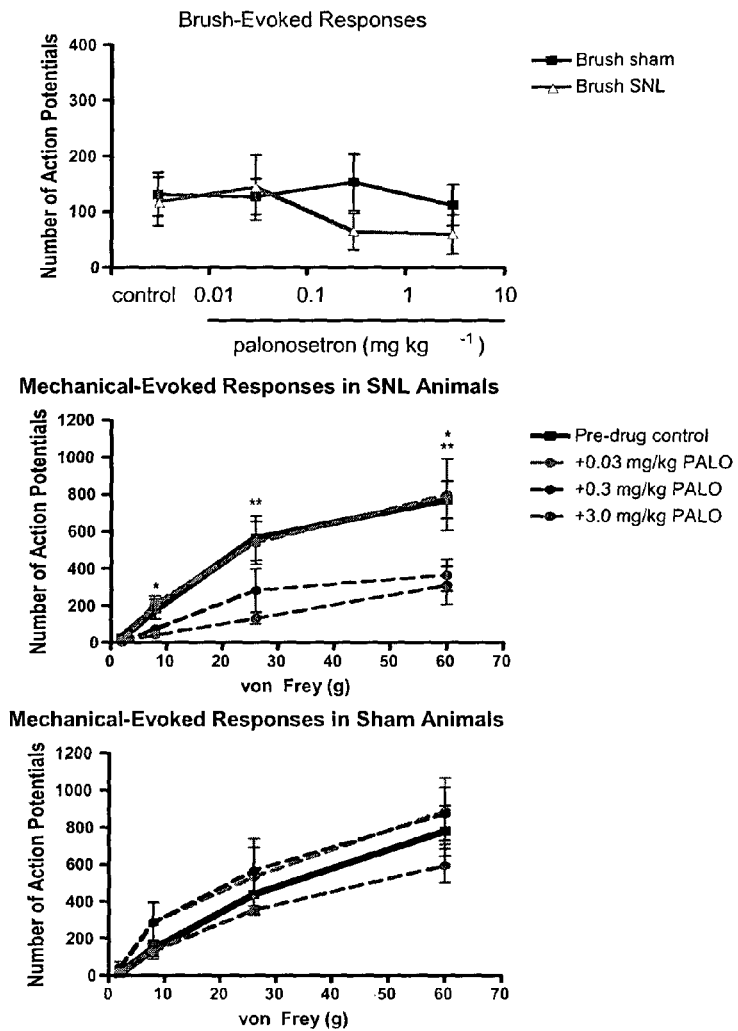
Fig.5. A comparison of the effects of Palonosetron (0.03, 0.3 and 3mg/kg s.c.) on the dynamic brush and mechanical punctate evoked responses of spinal dorsal horn neurones in sham and SNL. Data are expressed as the mean percentage of pre-drug control values ± S.E.M.

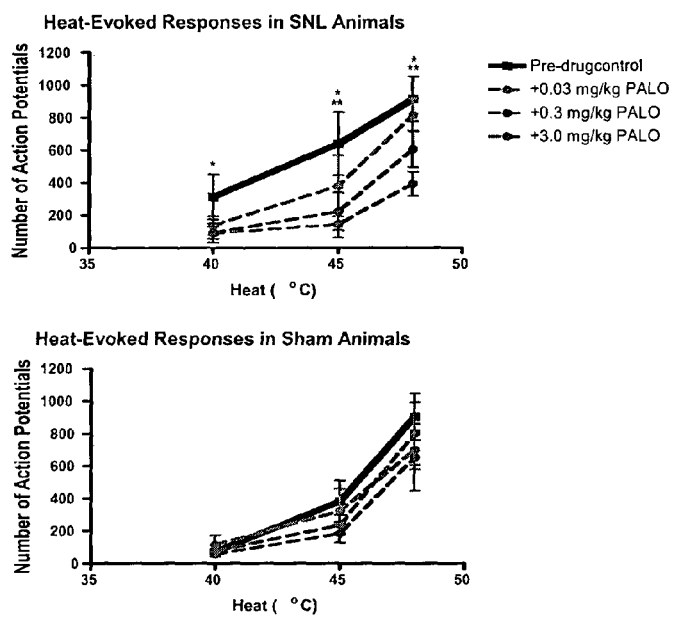
Fig.6. Comparison of the effects of Palonosetron (0.03, 0.3 and 3mg/kg s.c.) on the thermal evoked responses of spinal dorsal horn neurones in sham and SNL. Data are expressed as the mean percentage of pre-drug control values ± S.E.M.

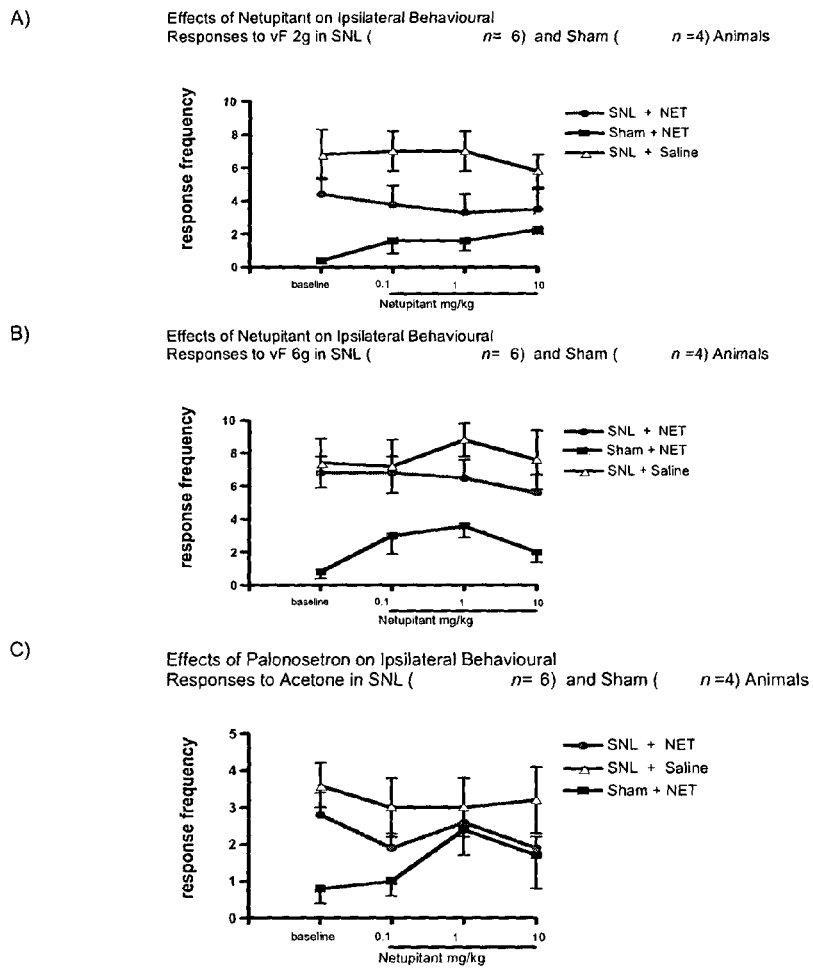
Fig. 7. Effects of netupitant on the number of withdrawal responses to A) vF2g, B) vF6g and C) acetone (cooling stimuli). In SNL rats, 1mg/kg appears to inhibit behavioral hypersensitivities.

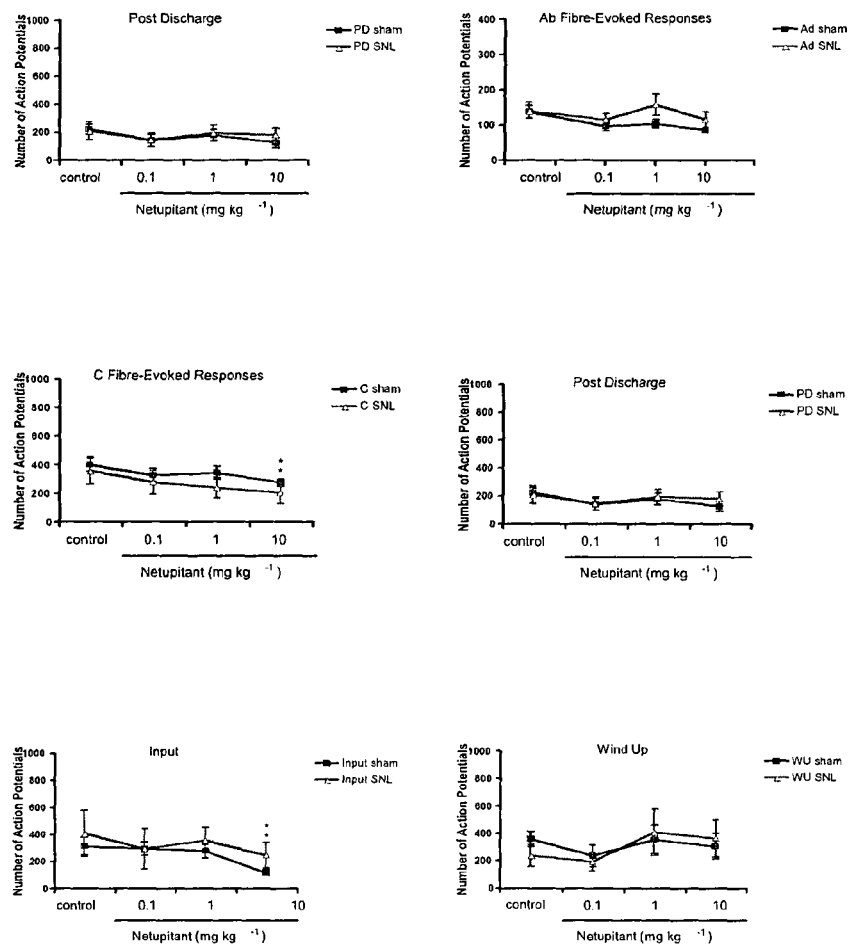
Fig. 8. A comparison of the effects of 3 doses of netupitant (0.1, 1 and 10mg/kg s.c) on the electrical responses of spinal dorsal horn neurones in sham and SNL rats. Data are expressed as the mean percentage of pre-drug control values ± S.E.M.

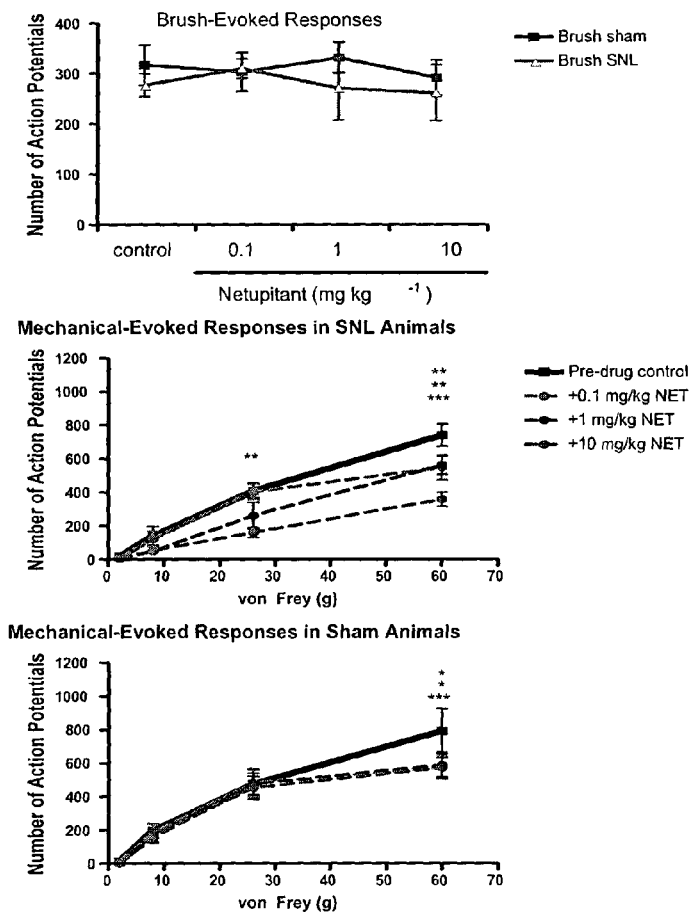
Fig. 9. A comparison of the effects of 3 doses of netupitant (0.1, 1 and 10mg/kg s.c) on the dynamic brush and mechanical punctate evoked responses of spinal dorsal horn neurones in sham and SNL rats. Data are expressed as the mean percentage of pre-drug control values ± S.E.M.

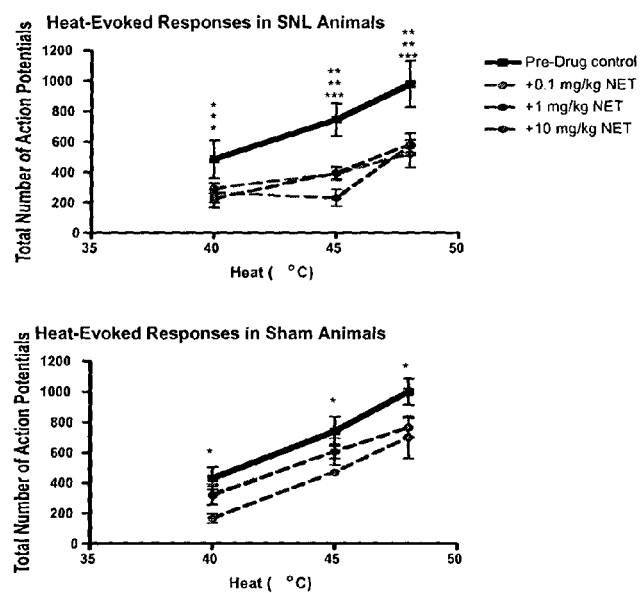
Fig. 10. A comparison of the effects of 3 doses of netupitant (0.1, 1 and 10mg/kg s.c) on the thermal evoked responses of spinal dorsal horn neurones in sham and SNL rats. Data are expressed as the mean percentage of pre-drug control values ± S.E.M.

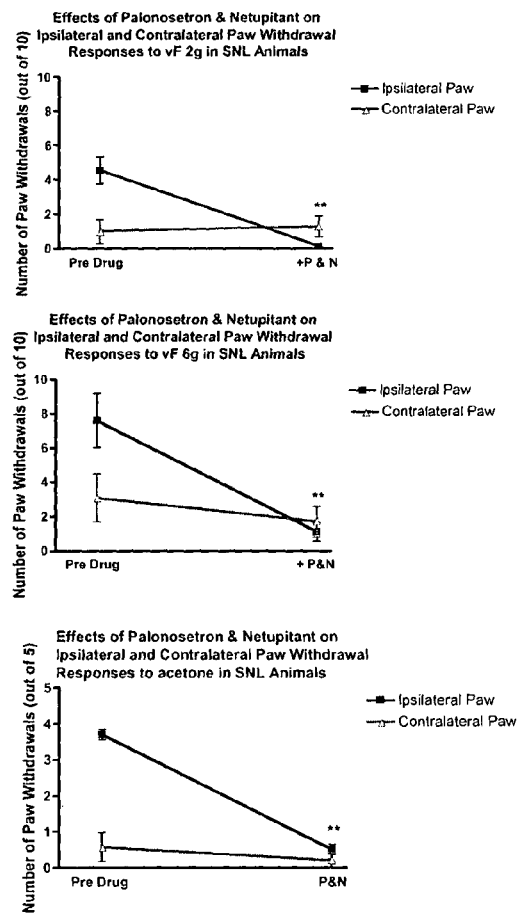
Fig. 11. Comparison of the effects of a combination of palonosetron (0.03 mg/kg s.c) and netupitant (0.1 mg/kg s.c.) on the number of withdrawal responses in the ipsilateral and contralateral paws to A) vF2g, B) vF6g and C) acetone (cooling stimuli) in SNL rats.

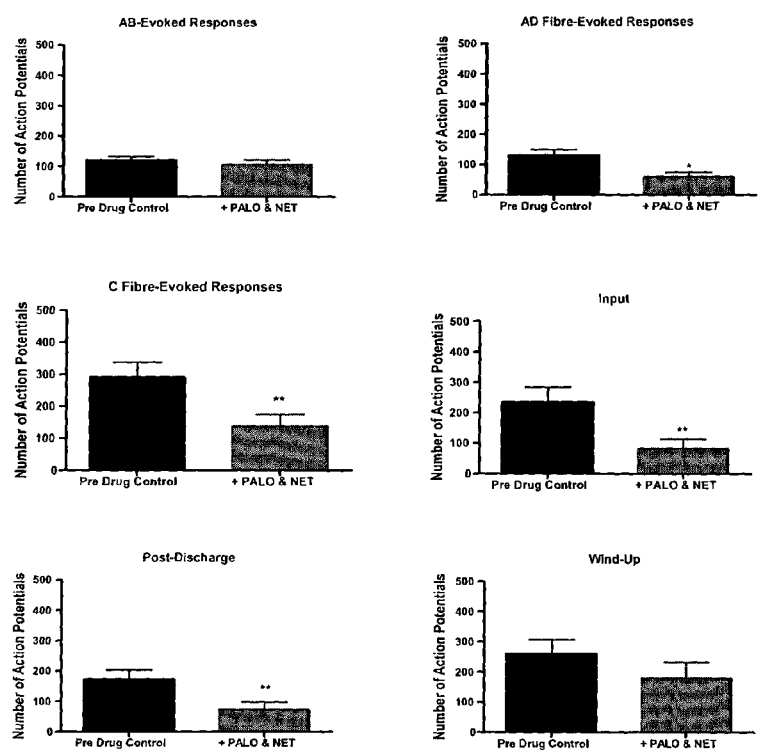
Fig. 12. Comparison of the effects of a combination of palonosetron (0.03 mg/kg s.c) and netupitant (0.1 mg/kg s.c.) on the electrical responses of spinal dorsal horn neurones in sham and SNL rats. Data are expressed as the mean percentage of pre-drug control values ± S.E.M.

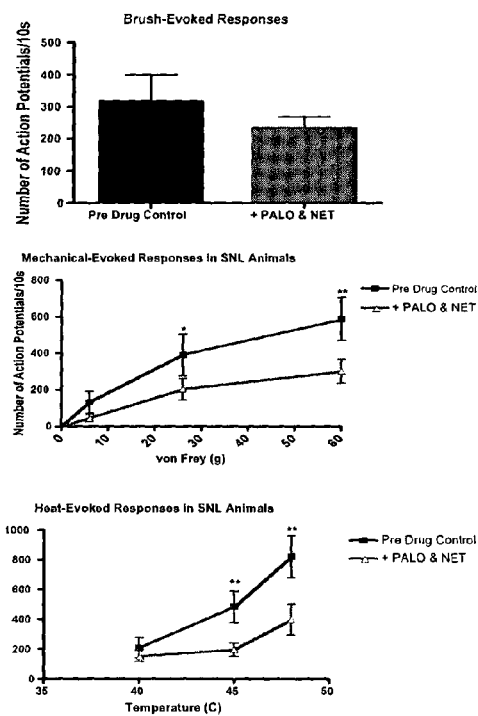
Fig. 13. Comparison of the effects of a combination of palonosetron (0.03 mg/kg s.c) and netupitant (0.1 mg/kg s.c.) on the dynamic brush, mechanical punctate and heat evoked responses of spinal dorsal horn neurones in SNL rats. Data are expressed as the mean percentage of pre-drug control values ± S.E.M.

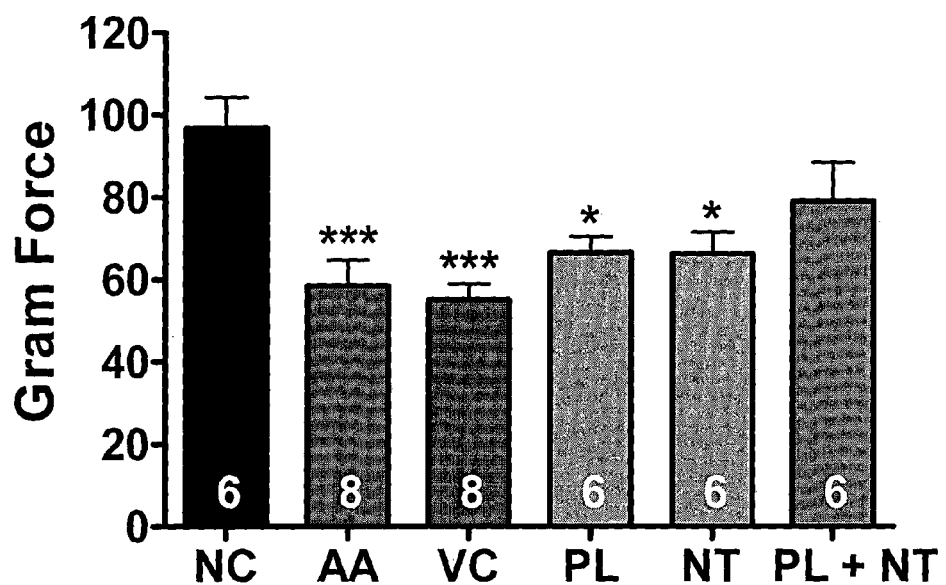
Figure 14: Palonosetron and Netupitant dosed in combination at 0.001 mg/kg showed a non-significant trend to inhibit AA-induced somatic hypersensitivity.
*compared to NC or •compared to VC or AA: One-way ANOVA with Bonferroni post-test

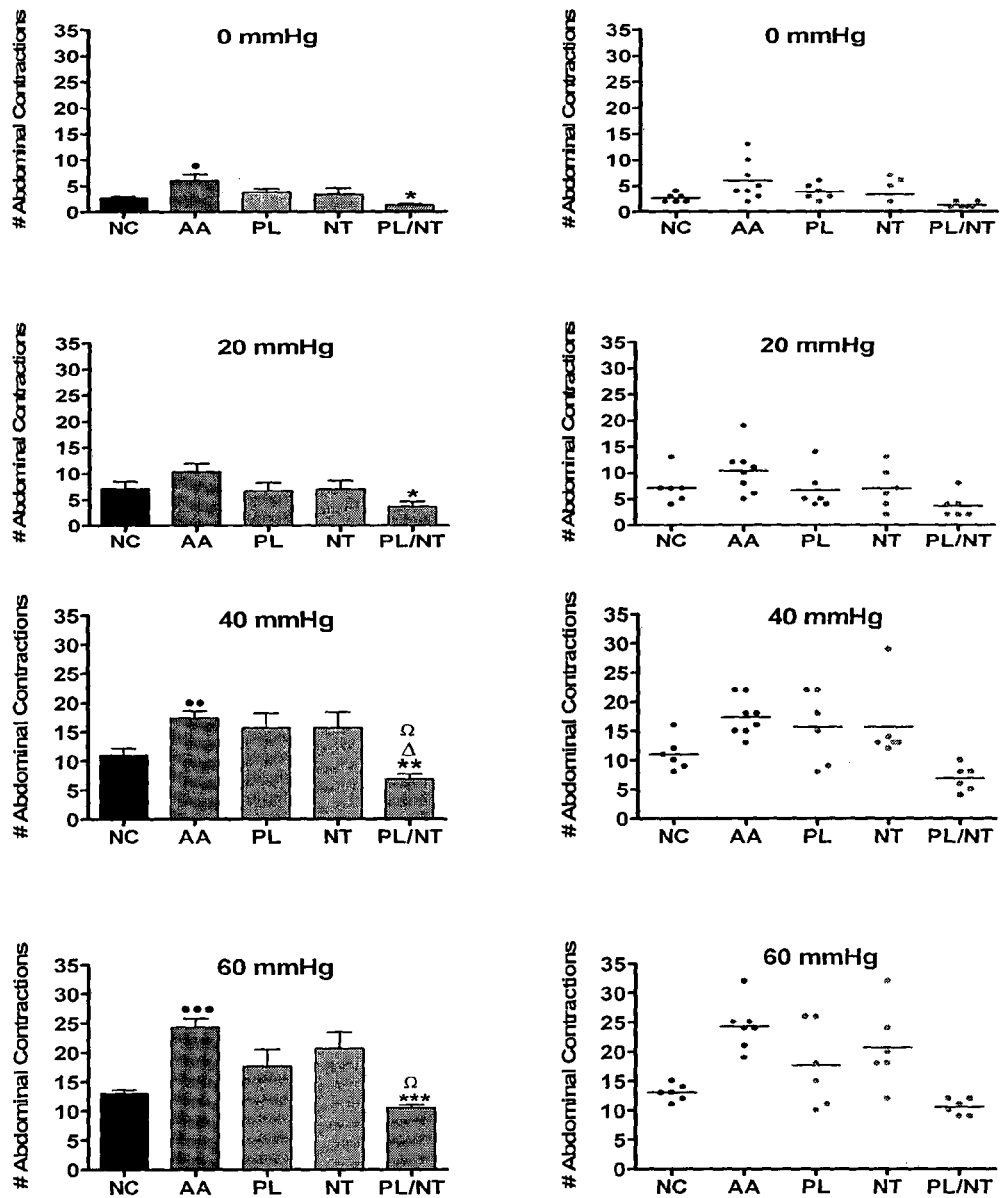
Figure 15: Visceral sensitivity results presented as individual distension pressure histograms with accompanying scatter-plot comparisons. Palonosetron or Netupitant dosed at 0.001 mg/kg p.o alone or in combination.
*compared to AA; •compared to NC; Ω compared to NT: One-way ANOVA with Bonferroni post-test

THERAPEUTIC COMBINATIONS OF NETUPITANT AND PALONOSETRON

CROSS-REFERENCE TO RELATED APPLICATIONS

This application is the U.S. national phase under 35 U.S.C. 371 of International Application No. PCT/IB2012/002013, filed on Oct. 10, 2012 (published as WO/2013/057554 on Apr. 25, 2013), which claims the benefit of U.S. Provisional Application No. 61/548,514, filed Oct. 18, 2011, all of which are herein incorporated by reference in their entirety.

FIELD OF THE INVENTION

The present invention relates to combinations of netupitant and palonosetron, and to methods of treating pain and irritable bowel syndrome (IBS) using such combinations.

BACKGROUND OF THE INVENTION

Palonosetron is a selective 5-HT3 antagonist marketed commercially as Aloxi® for the treatment of emesis. The chemical name of the compound is (3aS)-2-[(S)-1-Azabicyclo[2.2.2]oct-3-yl]-2,3,3a,4,5,6-hexahydro-1-oxo-1Hberiz[de]isoquinoline, as depicted by the following chemical structure of the hydrochloride salt:

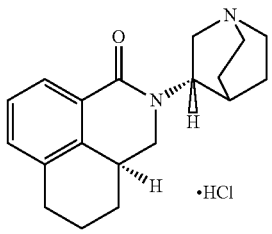 [SMILES: O=C1c2cccc3c2[C@H](CCC3)CN1[C@@H]1CN2CCC1CC2 ; Cl]

Methods of synthesizing palonosetron are described in U.S. Pat. Nos. 5,202,333 and 5,510,486. Pharmaceutically acceptably dosage forms are described in PCT publications WO 2004/067005 and WO 2008/049552 from Helsinn Healthcare.

Netupitant is a selective $NK_1$ receptor antagonist of the formula 2-[3,5-bis(trifluoromethyl)phenyl]-N,2-dimethyl-N-[4-(2-methylphenyl)-6-(4-methylpiperazin-1-yl)pyridin-3-yl]propanamide, or Benzeneacetamide, N,α,α-trimethyl-N-[4-(2-methylphenyl)-6-(4-methyl-1-piperazinyl)-3-pyridinyl]-3,5-bis(trifluoromethyl)-, having the below chemical structure:

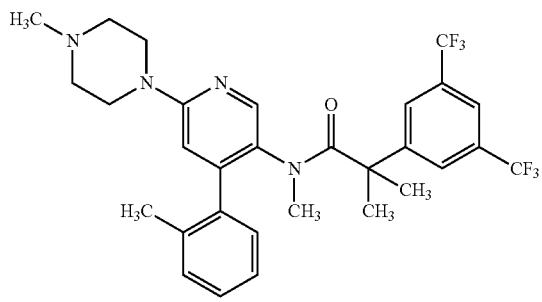 [SMILES: Cc1ccccc1-c1cc(N2CCN(C)CC2)ncc1N(C)C(=O)C(C)(C)c1cc(C(F)(F)F)cc(C(F)(F)F)c1]

Methods of synthesizing and formulating netupitant and its prodrugs are described in U.S. Pat. Nos. 6,297,375, 6,719,996 and 6,593,472 to Hoffmann La Roche.

Several prior art references disclose the combined use of an NK1 receptor antagonist and a 5-HT3 receptor antagonist for the treatment of emesis. Roila et al. report that the co-administration of a NK1 receptor antagonist, such as aprepitant, at the same time as a 5-HT3 antagonist, significantly increases the efficacy of 5-HT3 antagonists in preventing both acute and delayed CINV. See Roila F, Fatigoni S (2006) NEW ANTI-EMETIC DRUGS. *Ann Oncol* 17 Suppl 2: ii96-100. Roche reported in 2006 that "[s]ince 5HT3 and NK1 receptor antagonists exert additive effects [on nausea and vomiting] there is considerable potential for the combined use of Aloxi and netupitant." See NK1 receptor antagonists by Roche, Feb. 23, 2006, http://www.hospitalpharma.com/Features/feature.asp?RO-W_ID=742.

Palonosetron and other 5HT3 receptor antagonists were developed originally for the prevention of emesis, but more recently have received attention for their role in pain signaling and transmission in the peripheral and central nervous systems. 5HT3 receptors are known to mediate a descending facilitatory influence on spinal cord activity, a constituent drive that is particularly prominent on mechanical and chemical evoked activity. There is enhancement of this activity following peripheral nerve injury, spinal cord injury and after intense chemical stimulation. A number of studies using opioid-induced-hyperalgesia and activation of ERK support the concept of descending 5HT3 facilitation as a target for pain control. See, e.g., G H McCleane, et al., ANETH ANALG 2003; 97: 1474-8 (reporting that "5HT3 receptors play a pronociceptive role and mediate descending excitatory controls that allow spinal neurons to fully code peripheral stimuli.")

Spinal NK1 receptors are part of the post-synaptic targets for neurotransmitter released from afferent terminals, and also have been studied for their role in pain. See De Felipe C, et al. (March 1998) NATURE 392 (6674): 394-7 (reporting that "the peptide neurotransmitter substance P modulates sensitivity to pain by activating the neurokinin-1 (NK-1) receptor, which is expressed by discrete populations of neurons throughout the central nervous system.") L M Thomson et al. (2008 January) J PAIN; 9(1): 11-19 (reporting that substance P systems "may also represent important therapeutic targets for the retention and restoration of pain relief with prolonged morphine treatment.")

Only about 15% of afferents release substance P and this may be reduced after nerve injury although some studies report a phenotypic switch of the transmitter to large fibers. Thus, while several prior art references implicate NK1 receptors in the pain signaling process, considerable doubt has emerged as to the viability of NK1 receptor antagonists to successfully treat pain in human patients. As Hill stated in 2000, "NK1 receptor antagonists have failed to exhibit efficacy in [human] clinical trials of a variety of clinical pain states." See R Hill (July 2000) TRENDS IN PHARMACEUTICAL SCIENCES Vol. 21, pages 244-246. So, the target alone might not be relevant in controlling the pain processing.

Irritable bowel syndrome (IBS), a functional bowel disorder, is a syndrome characterized by abdominal discomfort or pain associated with defecation and abnormal bowel movement in spite of the absence of a detectable intestinal organic disease. The symptoms include diarrhea, abdominal pain, abdominal bloating, and constipation, and are classified into a diarrhea type (IBS-D), a constipation type (IBS-C), and an alternating diarrhea and constipation type (IBS-A). The symptoms may be accompanied by a psychological condition such as anxiety, hypersensitivity, tension, fretfulness, depression, or the like.

The precise pathophysiology of IBS remains to be elucidated. Nevertheless, there is a heightened sensitivity to visceral pain perception, known as peripheral sensitization. This sensitization involves a reduction in the threshold and an increase in the gain of the transduction processes of primary afferent neurons, attributable to a variety of mediators including monoamines (e.g., catecholamines and indoleamines), substance P, and a variety of cytokines and prostanoids such as E-type prostaglandins (see, e.g., Mayer et al., Gastroenterol., 107:271-293 (1994)). Also implicated in the etiopathology of IBS is intestinal motor dysfunction, which leads to abnormal handling of intraluminal contents and/or gas (see, e.g., Kellow et al., Gastroenterol., 92:1885-1893 (1987); Levitt et al., Ann. Int. Med., 124:422-424 (1996)). Psychological factors may also contribute to IBS symptoms appearing in conjunction with, if not triggered by, disturbances including depression and anxiety (see, e.g., Drossman et al., Gastroenterol. Int., 8:47-90 (1995)).

Although no animal models of IBS exist, advances in the understanding of the pathophysiology of IBS have facilitated the development of preclinical rodent models of visceral hypersensitivity. The method of colorectal distention (CRD) can be used to activate nociceptive neuronal pathways from the gastrointestinal (GI) tract, which induces a protective reflex of abdominal muscle contraction (see, e.g., Ness et al., Brain Research, 450: 153-169 (1988)). One method of measuring these contractions is via strain gauges sutured onto the abdominal muscle (see, e.g., Plourde et al., American Journal of Physiology, 273: G191-196 (1997)). Colonic hypersensitivity can be induced experimentally in a rodent model by infusing dilute acetic acid (0.6%) into the colon which causes a transient sensitization of colonic sensory afferents which results in an increase in the VMR to CRD (see e.g., Gaudreau et al., Neuroscience Letters, 351 (2): 59-62 (2003); Venkova et al., Toxicology and Applied Pharmacology, 196: 215-222 (2004)). Although heightened visceral pain perception is well demonstrated in IBS, the existence of abnormalities in somatic pain is controversial with more recent reports suggesting enhanced somatic sensitivity in IBS through viscerosomatic convergence at the level of the spinal cord (see e.g., Chang, Gastroenterology Clinics of North America, 34 (2): 271-2792005; Zhou et al., Pain, 148 (3): 454-461 (2010)).

The gastrointestinal function is highly regulated by the nerves, and a variety of receptors are present. Therefore, an anticholinergic agent, an antidiarrheal, or a laxative is administered according to the gastrointestinal symptoms such as an abdominal pain, diarrhea, and constipation, and an antidepressant or an antianxiety agent is used if needed. Although alosetron HCl, a serotonin $5-HT_3$ receptor antagonist, is known as a therapeutic agent for diarrhea-type IBS (IBS-D), this agent is applied only to woman patients with severe symptoms because serious gastrointestinal disorders, particularly ischemic colitis and serious constipation, are observed. Further, although tegaserod maleate, a serotonin $5-HT_4$ receptor agonist, is known as a therapeutic agent for constipation-type IBS (IBS-C), this agent is applied only to women patients. In addition, lubiprostone, a ClC-2 chloride channel activator, is applied only to women patients for constipation-type IBS (IBS-C). Further, Cilansetron, another selective $5-HT_3$ antagonist, is currently in clinical trials in Europe for the treatment of IBS-D in both men and women; however, in 2005, the sponsor of cilansetron withdrew its application for approval from the US FDA on the basis of a "non-approvable" letter (additional clinical trials were requested). Therefore, the therapeutic options of IBS are limited as the current treatments are gender and IBS subtype specific, and have significant side effects. Therefore, a novel therapeutic agent and method for IBS with no gender or subtype difference and with reduced side effects is strongly desired.

SUMMARY OF THE INVENTION

Consistent with other human studies reported in the prior art, applicant has determined that netupitant has a very marginal effect on the treatment of neuropathic pain. In particular, netupitant exhibits zero or minimal effect when tested in animal models of allodynia/neuropathic pain. However, when the netupitant is added to palonosetron in therapeutically effective amounts, the netupitant acts synergistically with the palonosetron, and produces a much greater reduction in pain than when the palonosetron is administered alone.

The opposite effect is observed when the compounds are evaluated against various electrophysiological measures of pain control. In the course of these experiments, the inventors have discovered that netupitant has an independent effect, and that palonosetron exhibits zero or minimal effect. However, when the palonosetron is added to netupitant in therapeutically effective amounts, the palonosetron acts synergistically with the netupitant, and induces much greater control over electrophysiological measures of pain than when the netupitant is administered alone.

Therefore, in one embodiment, the invention provides a synergistic drug combination comprising (a) palonosetron or a pharmaceutically acceptable salt or prodrug thereof; and (b) netupitant or a pharmaceutically acceptable salt or prodrug thereof, in synergistically effective amounts. Various measures can be used to determine whether the amounts in the drug combination are synergistic. In a preferred embodiment, the amounts are synergistically effective when administered to a 70 kg human based on one or more measures selected from (a) the treatment of mechanically evoked allodynia, (b) the modulation of electrically-evoked dorsal horn neural C-fiber responses, and (c) the modulation of electrically-evoked dorsal horn neural AD-fiber responses. An orally-administered combination drug product that contains from 0.01 to 1.0 mg of palonosetron and from 10 to 300 mg of netupitant has been shown to demonstrate synergy under one or more of these criteria.

In another embodiment, the invention is based on the discovery that netupitant and palonosetron work together to treat chronic neuropathic pain, and that they produce a greater therapeutic effect when used together than when either is administered alone. Therefore, the invention also provides a method of treating chronic neuropathic pain comprising administering to a human patient in need thereof a drug combination comprising palonosetron and netupitant, or their pharmaceutically acceptable salts or prodrugs, in therapeutically effective amounts. The combination is preferably administered orally, and preferably includes from 0.01 to 1.0 mg of palonosetron and from 10 to 300 mg of netupitant administered on a daily basis. In a preferred embodiment, the method is used to treat diabetic peripheral neuropathic pain, fibromyalgia, or post-herpetic neuralgia.

Further, applicants have determined that palonosetron, netupitant, or a combination of palonosetron and netupitant is effective in treating pain associated with Irritable bowel syndrome (IBS). Specifically, applicants have determined that a combination of a sub-therapeutic dose of palonosetron and a sub-therapeutic dose of netupitant has a synergistic effect in treating a model of Irritable bowel syndrome. Therefore, in one embodiment, the invention provides a synergistic drug combination comprising (a) a sub-therapeutic dose of palonosetron or a pharmaceutically acceptable salt or prodrug thereof; and (b) a sub-therapeutic dose of netupitant or a pharmaceutically acceptable salt or prodrug thereof, in synergistically effective amounts. In another embodiment, the invention provides a method of treating Irritable bowel syndrome comprising administering to a human patient in need thereof a synergistic effective combination comprising (a) a sub-therapeutic dose of palonosetron or a pharmaceutically acceptable salt or prodrug thereof; and (b) a sub-therapeutic dose of netupitant or a pharmaceutically acceptable salt or prodrug thereof, in synergistically effective amounts. The drug combinations and methods disclosed in the present invention have advantages over the prior art, e.g., they are not gender specific or IBS-subtype specific, and less side effects are associated with the drug combinations and methods.

BRIEF DESCRIPTION OF THE DRAWINGS

FIG. 1 is a series of graphs depicting the temporal development of mechanical and thermal hypersensitivity post nerve injury. Nerve injury induced a significant increase in the number of paw withdrawals to A) vf 2 g, B) vF 6 g and C) acetone stimulation of the ipsilateral hind paw compared with the responses seen in sham controls.

FIG. 2 is a series of graphs depicting the effects of palonosetron on the number of paw withdrawals to A) vf 2 g, B) vF 6 g and C) acetone. A dose related reduction in paw withdrawal frequency is seen in the SNL rats only.

FIG. 3 is a graph comparing the total time spent by SNL and Sham rats on a rotarod. Palonosetron (0.03, 0.3 and 3 mg/kg) did not impair motor performance in either group. Data are presented as mean±SEM.

FIG. 4 is a series of graphs comparing the effects of Palonosetron (0.03, 0.3 and 3 mg/kg s.c.) on the electrical evoked responses of spinal dorsal horn neurones in sham and SNL rats. Data are expressed as the mean percentage of pre-drug control values±S.E.M.

FIG. 5 is a series of graphs comparing of the effects of Palonosetron (0.03, 0.3 and 3 mg/kg s.c.) on the dynamic brush and mechanical punctate evoked responses of spinal dorsal horn neurones in sham and SNL rats. Data are expressed as the mean percentage of pre-drug control values±S.E.M.

FIG. 6 is a series of graphs comparing the effects of Palonosetron (0.03, 0.3 and 3 mg/kg s.c.) on the thermal evoked responses of spinal dorsal horn neurones in sham and SNL. Data are expressed as the mean percentage of pre-drug control values±S.E.M.

FIG. 7 is a series of graphs depicting the effects of netupitant on the number of withdrawal responses to A) vF2 g, B) vF6 g and C) acetone (cooling stimuli). In SNL rats, 1 mg/kg appears to inhibit behavioral hypersensitivities.

FIG. 8 is a series of graphs comparing the effects of 3 doses of netupitant (0.1, 1 and 10 mg/kg s.c) on the electrical responses of spinal dorsal horn neurones in sham and SNL rats. Data are expressed as the mean percentage of pre-drug control values±S.E.M.

FIG. 9 is a series of graphs comparing the effects of 3 doses of netupitant (0.1, 1 and 10 mg/kg s.c) on the dynamic brush and mechanical punctate evoked responses of spinal dorsal horn neurones in sham and SNL rats. Data are expressed as the mean percentage of pre-drug control values±S.E.M.

FIG. 10 is a series of graphs comparing the effects of 3 doses of netupitant (0.1, 1 and 10 mg/kg s.c) on the thermal evoked responses of spinal dorsal horn neurones in sham and SNL rats. Data are expressed as the mean percentage of pre-drug control values±S.E.M.

FIG. 11 is a series of graphs comparing the effects of a combination of palonosetron (0.03 mg/kg s.c) and netupitant (0.1 mg/kg s.c.) on the number of withdrawal responses in the ipsilateral and contralateral paws to A) vF2 g, B) vF6 g and C) acetone (cooling stimuli) in SNL rats.

FIG. 12 is a series of graphs comparing the effects of a combination of palonosetron (0.03 mg/kg s.c) and netupitant (0.1 mg/kg s.c.) on the electrical responses of spinal dorsal horn neurones in sham and SNL rats. Data are expressed as the mean percentage of pre-drug control values±S.E.M.

FIG. 13 is a series of graphs comparing the effects of a combination of palonosetron (0.03 mg/kg s.c) and netupitant (0.1 mg/kg s.c.) on the dynamic brush, mechanical punctate and heat evoked responses of spinal dorsal horn neurones in SNL rats. Data are expressed as the mean percentage of pre-drug control values±S.E.M.

FIG. 14 shows that Palonosetron and Netupitant dosed in combination at 0.001 mg/kg showed a non-significant trend to inhibit AA-induced somatic hypersensitivity.

FIG. 15 is a series of graphs where visceral sensitivity results presented as individual distension pressure histograms with accompanying scatter-plot comparisons. Palonosetron or Netupitant dosed at 0.001 mg/kg p.o alone or in combination.

DETAILED DESCRIPTION OF THE INVENTION

The present invention may be understood more readily by reference to the following definitions and detailed description of preferred embodiments of the invention and the non-limiting Examples included therein.

The pharmaceutically acceptable salts of netupitant and palonosetron, as well as their pharmaceutically acceptable prodrugs can be used in the methods and compositions of the present invention. As used herein, the term "pharmaceutically acceptable salt" refers to a salt of a compound to be administered prepared from pharmaceutically acceptable non-toxic acids. Examples of suitable inorganic acids are hydrochloric, hydrobromic, hydroiodic, nitric, sulfuric, and phosphoric. Suitable organic acids may be selected from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

The term "prodrug" refers to a chemical derivative of an active ingredient that degrades to the active ingredient in vivo via spontaneous or enzymatic transformation. Prodrugs are designed to overcome pharmaceutically and/or pharmacokinetically based problems associated with the parent drug molecule that might otherwise limit the clinical usefulness of the drug, especially due to drug solubility issues in the case of netupitant. Prodrugs of netupitant are described in U.S. Pat. No. 6,593,472, the contents of which are hereby incorporated by reference.

When dose amounts are expressed herein in reference to a salt or prodrug of an active ingredient, it will be understood that the amount expressed is based on the corresponding amount of the free base of the ingredient. Thus, for a prodrug with a molecular weight of 600, if this document referred to the administration of 100 mg of netupitant or a prodrug thereof, it would be understood that 125.36 mg of the prodrug is administered, since the molecular weight of the prodrug is 125.36% of the molecular weight of the netupitant base.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

The terms "treating" and "treatment," when used herein, refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "significantly" refers to a level of statistical significance. The level of statistical significant can be, for example, of at least p<0.05, of at least p<0.01, of at least p<0.005, or of at least p<0.001. When a measurable result or effect is expressed or identified herein, it will be understood that the result or effect can be evaluated based upon its statistical significance relative to a baseline, typically placebo based.

Throughout the description and claims of this specification, the word "comprise" and variations of the word, such as "comprising" and "comprises," means "including but not limited to," and is not intended to exclude, for example, other additives, components, integers or steps.

When the singular forms "a," "an" and "the" or like terms are used herein, they will be understood to include plural referents unless the context clearly dictates otherwise. Thus, for example, reference to "a pharmaceutical carrier" includes mixtures of two or more such carriers, and the like. The word "or" or like terms as used herein means any one member of a particular list and also includes any combination of members of that list.

When ranges are given by specifying the lower end of a range separately from the upper end of the range, it will be understood that the range can be defined by selectively combining any one of the lower end variables with any one of the upper end variables that is mathematically possible.

When used herein the term "about" or "ca." will compensate for variability allowed for in the pharmaceutical industry and inherent in pharmaceutical products, such as differences in product strength due to manufacturing variation and time-induced product degradation. The term allows for any variation which in the practice of pharmaceuticals would allow the product being evaluated to be considered bioequivalent to the recited strength of a claimed product.

Methods of Treatment

As discussed above, it has now been discovered that palonosetron and netupitant are therapeutically effective, and synergistically effective under some circumstances, to treat pain, particularly chronic neuropathic pain. Therefore, in one embodiment, the invention provides a synergistic drug combination comprising (a) palonosetron or a pharmaceutically acceptable salt or prodrug thereof; and (b) netupitant or a pharmaceutically acceptable salt or prodrug thereof, in synergistically effective amounts.

In another embodiment, the invention is based on the discovery that netupitant and palonosetron work together to treat neuropathic pain, and that they produce a greater therapeutic effect when used together than when either is administered alone. Therefore, the invention also provides a method of treating neuropathic pain comprising administering to a human patient in need thereof a drug combination comprising palonosetron and netupitant, in therapeutically effective amounts.

While the methods can be used to treat various forms of pain, including nociceptive and neuropathic pain, chronic or acute, in a preferred embodiment the methods are used to treat chronic neuropathic pain (e.g. pain persisting for more than three, six or twelve months). In an even more preferred embodiment, the pain is chronic neuropathic pain characterized by one, two or three or more symptoms selected from burning pain, paresthesia/dysesthesia, shooting/lancinating pain, numbness, hyperalgesia and allodynia.

The pain can be inherited, or it may be acquired. Acquired peripheral neuropathies are grouped into three broad categories: those caused by systemic disease, those caused by trauma from external agents, and those caused by infections or autoimmune disorders affecting nerve tissue, and each of these categories can be treated using the methods of the current invention.

Causes of acquired peripheral neuropathy that can be treated using the methods of this invention include physical injury (trauma) to a nerve, tumors, toxins, autoimmune responses, nutritional deficiencies, alcoholism, and vascular and metabolic disorders. Drugs known to induce neuropathies treatable by the current methods include anti-virals such as ddI and ddC, phenyloin, isoniazid, vincristine, high dose vitamins, and folic acid antagonists.

The neuropathic pain treated using the methods of this invention can also be characterized as peripheral or central. Peripheral neuropathies that can be treated by the methods of the current invention include those originating from diabetes, post herpetic neuralgia, fibromyalgia, and physical injuries to the nervous system such as spinal cord injury.

Diabetic peripheral neuropathic pain (DPNP) is a preferred indication for the methods of the current invention. DPNP may result from type I or type II diabetes mellitus, and is preferably defined by a diagnosis of painful distal symmetrical sensorimotor polyneuropathy; and a pain score≥4 on an eleven point scale ranging from zero (no pain) to 10 (worst possible pain)).

Fibromyalgia is another preferred indication for the methods of the current invention. This disease is preferably defined as a history of widespread pain for three months, and pain present at 11 or more of the 18 specific tender point sites on digital palpation with an approximate force of 4 kg., as defined by the American College of Rheumatology criteria for fibromyalgia. See Wolfe F et al. ARTHRITIS RHEUM 1990; 33:160-72. The 18 sites include the occiput (bilateral, at the suboccipital muscle insertions), the low cervical (bilateral, at the anterior aspects of the intertransverse spaces at C5-C7), the trapezius (bilateral, at the midpoint of the upper border), the supraspinatus (bilateral, at origins, above the scapula spine near the medial border), the second rib (bilateral, at the second costochondral junctions, just lateral to the junctions on upper surfaces), the lateral epicondyle (bilateral, 2 cm distal to the epicondyles), the gluteal (bilateral, in upper outer quadrants of buttocks in anterior fold of muscle), the greater trochanter (bilateral, posterior to the trochanteric prominence), and the knee (bilateral, at the medial fat pad proximal to the joint line).

In a distinct embodiment, the methods of the present invention are used to treat neuropathic pain characterized by pain at one or a combination of the foregoing specific tender point sites.

Yet another preferred indication for the methods of the current invention is post-herpetic neuralgia, which may be defined as neuralgia persisting for at least three months following healing of herpes zoster rash.

A preferred measure of the success of any treatment is a statistically significant improvement in the number of patients having at least a 50% improvement in pain score from baseline, relative to placebo. The pain score is preferably derived from an eleven point scale ranging from zero (no pain) to 10 (worst possible pain)).

Several other features can also be used to characterize the pain or patients treated by the methods of this invention, regardless of the type or source of pain, or the clinical indication involved. Thus, in one embodiment the pain or patient is unresponsive to one or more analgesic drugs selected from opioid analgesics, non-steroidal anti-inflammatory drugs (NSAIDs), tricyclic antidepressants (TCA) such as amitriptyline, and anticonvulsants such as gabapentin, phenyloin, and carbamazepine. In another embodiment, the pain is accompanied by a comorbid diagnosis of major depressive disorder (MDD), anxiety and/or depression.

Other analgesics can be administered as part of the methods of the current invention, including acetaminophen (up to 4 g/day), an opioid analgesic, or an NSAID.

The dosage can vary within wide limits and will, of course, be fitted to the individual requirements in each particular case. In general, in the case of oral administration a daily dosage of palonosetron of from about 0.01 or 0.05 to about 0.5 or 2.0 mg per person should be appropriate, alternatively from about 0.01 or 0.05 to about 1.0 mg., and alternatively from about 0.025 mg to about 0.5 mg. The dose can be administered in a single daily dosage, due to the excellent pharmacokinetics observed for the molecule, although multiple doses could also be administered (i.e. two or three times daily). With respect to palonosetron, these doses should be substantially the same whether administered orally or via injection.

In the case of oral administration of netupitant, a daily dosage of netupitant of from about 10 to about 300 mg should be appropriate, preferably from about 20 to about 200 mg, or from about 30 to about 150 mg. Once again, it is preferred to administer this dose just once daily, although it is possible to divide the daily dose into two or three doses. In the case of injection, the dose would constitute about 40% of the oral dose, and the foregoing ranges can be adjusted to 40%.

Various measures can be used to determine whether the amounts in the drug combination are synergistic. In a preferred embodiment, the amounts are synergistically effective when administered once daily to a 70 kg human based on one or more measures selected from (a) the treatment of mechanically evoked allodynia, (b) the modulation of electrically-evoked dorsal horn neural C-fiber responses, and (c) the modulation of electrically-evoked dorsal horn neural AD-fiber responses. Combination drug products that contain the amounts of palonosetron and netupitant described herein have been shown to demonstrate synergy under one or more of these criteria.

Further, it has now been discovered that palonosetron, netupitant or a combination of palonosetron and netupitant are effective to treat irritable bowel syndrome (IBS). In a particularly preferred embodiment, applicants have determined that a combination of a sub-therapeutic dose of palonosetron and a sub-therapeutic dose of netupitant has a synergistic effect in treating Irritable bowel syndrome. Sub-therapeutic dose refers to a dose which is ineffective against IBS when administered alone. Therefore, in one embodiment, the invention provides a method of treating Irritable bowel syndrome comprising administering to a human patient in need thereof a synergistically-effective combination comprising (a) a sub-therapeutic dose of palonosetron or a pharmaceutically acceptable salt or prodrug thereof; and (b) a sub-therapeutic dose of netupitant or a pharmaceutically acceptable salt or prodrug thereof.

In another embodiment, the above disclosed methods are effective in treating one or more indications selected from the group consisting of alternating IBS (IBS-A), IBS with diarrhea (IBS-D) and IBS with constipation (IBS-C). The primary symptoms of said IBS-C are abdominal pain and constipation. Constipation can be evaluated by accessing stool frequency. The baseline of the abdominal pain can be defined as weekly average of worst abdominal pain in past 24 hours score of equal to or greater than 3.0 in a 0 to 10 point scale. The baseline of stool frequency can be defined as less than three complete spontaneous bowel movements (CSBM) per week. It has been discovered that the above disclosed methods can (1) decrease in weekly average of worst abdominal pain in past 24 hours score of equal to or greater than 30% compared with baseline; and (2) increase of one or more CSBM per week compared with baseline. Therefore, in another embodiment, the invention provides a method of treating Irritable bowel syndrome with constipation (IBS-C) where said method is effective in (1) decreasing intensity of said abdominal pain equal to or greater than 30 percent based on weekly average of worst abdominal pain in past 24 hours as compared with baseline; and (2) increasing at least one complete spontaneous bowel movements (CSBM) per week as compared with baseline.

The primary symptoms of IBS with diarrhea (IBS-D) are abdominal pain and diarrhea. Diarrhea can be evaluated by accessing stool consistency. Stool consistency is described according to the Bristol Stool Scale, which is a medical aid designed to classify the form of human faeces in seven categories. The seven types of stool according to the Bristol Stool Scale are: Type 1: Separate hard lumps, like nuts (hard to pass); Type 2: Sausage-shaped, but lumpy; Type 3: Like a sausage but with cracks on its surface; Type 4: Like a sausage or snake, smooth and soft; Type 5: Soft blobs with clear cut edges (passed easily); Type 6: Fluffy pieces with ragged edges, a mushy stool; and Type 7: Watery, no solid pieces. Entirely liquid. The baseline of the abdominal pain can be defined as weekly average of worst abdominal pain in past 24 hours score of equal to or greater than 3.0 in a 0 to 10 point scale. The baseline of stool consistency can be defined as weekly average equal to or greater than Type 6 Bristol Stool Scale (BSS). It has been discovered that the above disclosed methods can (1) decrease the weekly average of worst abdominal pain in past 24 hours by 30% or more compared with baseline; and (2) achieve a weekly average of equal to or less than Type 5 Bristol Stool Scale (<Type 2 BSS can be considered an adverse event). Therefore, in another embodiment, the invention provides a method of treating Irritable bowel syndrome with diarrhea (IBS-D) where said method is effective in (1) decreasing the intensity of abdominal pain by 30 percent or more based on a weekly average of worst abdominal pain in the previous 24 hours as compared with baseline; and (2) achieving a weekly average of equal to or less than Type 5 Bristol Stool Scale (<Type 2 BSS can be considered an adverse event).

As discussed above, the disclosed methods are non-specific to IBS subtypes. Further, it has been discovered that the above disclosed methods can be applied to both male and female patients. Therefore, in another embodiment, the invention provides a method of treating Irritable bowel syndrome wherein said method is not gender specific. Moreover, since the disclosed methods administer a combination of palonosetron and netupitant to patients where each agent is in sub-therapeutic dose, said methods significantly reduce the potential side effects. Therefore, in another embodiment, the invention provides a method of treating Irritable bowel syndrome wherein associated side effects are significantly reduced.

In another embodiment, the invention provides a method of treating Irritable bowel syndrome where said method is effective to treat other symptoms of IBS-C, e.g., abdominal discomfort, and other symptoms of IBS-D, e.g., abdominal discomfort and fecal incontinence. In still another embodiment, the invention provides a method of treating Irritable bowel syndrome (IBS) wherein said IBS is caused by colonic and/or somatic hypersensitivity. In another embodiment, the invention provides a method of treating Irritable bowel syndrome (IBS) wherein said method is effective in inhibiting said colonic and/or somatic hypersensitivity.

In another embodiment, the invention provides a method of treating Irritable bowel syndrome, comprising administering a palonosetron dose of less than 0.01 mg per kg body weight and a netupitant dose of less than 0.01 mg per kg body weight to a patient in need thereof. In still another embodiment, the invention provides a method of treating Irritable bowel syndrome, comprising administering a palonosetron dose of about 0.001 mg per kg body weight and a netupitant dose of about 0.001 mg per kg body weight to a patient in need thereof.

Pharmaceutical Compositions

Various pharmaceutical compositions can be developed that make use of the combinations described herein. The composition can be administered by any appropriate route, for example, orally, parenterally, or intravenously, in liquid or solid form.

Preferred modes of administrations of the active compounds are injectable and oral. These compositions will generally include an inert diluent or an edible carrier. They may be enclosed in gelatin capsules (for oral use) or compressed into tablets (for oral or buccal use) or formulated into troches (for buccal use). For these purposes, the active compound can be incorporated with excipients and used in the form of tablets, troches, or capsules. Pharmaceutically compatible binding agents, and/or adjuvant materials can be included as part of the composition.

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a gliding such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, orally disintegrating film, orally disintegrating tablet, chewing gum or the like. A syrup may contain, in addition to the active compounds, sucrose as a sweetening agent and certain preservatives, dyes and colorings and flavors.

Solutions or suspensions used for injection can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride, mannitol and dextrose. An injectable preparation can be enclosed in ampoules, disposable syringes or multiple dose vials made of glass or plastic.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Experiments were performed on male Sprague-Dawley rats, which were housed in cages under a 12-hour alternating light/dark cycle with ad libitum access to food and water. All animal experiments were approved by the United Kingdom Home Office and were carried out in accordance with guidelines set by personal and project licenses and thus complied with the UK Animals (Scientific Procedures) Act 1986. All efforts were made to minimise animal suffering and to reduce number of animals used.

SNL Surgery

A model of experimental neuropathic pain with symptoms of allodynia and hyperalgesia was established by tightly ligating the L5 and L6 spinal nerves as previously described (Kim and Chung, 1992). Within a sterile theatre, rats weighing approximately 130-150 g were anaesthetised (1:1 $O_2:N_2O$, 3% halothane for induction, 1% maintenance) and following a small left-side incision at approximately L4-S2, paraspinal muscle and fat was removed from spinous processes. Part of the L6 traverse process was clipped with rangeurs to expose the parallel-lying L4 and L5 spinal nerves. The L5 nerve was isolated and hooked with a finely-pulled glass rod and tightly tied with non-absorbable 6-0 silk thread distal to the dorsal root ganglion (and proximal to the formation of the sciatic nerve). The L6 nerve was then hooked from under the sacrum and tied in a similar way. Haemostasis was confirmed and the wound was sutured with 3-0 absorbable silk. The surrounding skin was pulled together and secured over the injury with wound clips. Rats recovered in an incubator, and once it had been confirmed that they had no observable motor impairment in their left hindpaw, were re-housed in cages as above.

Sham surgery was performed in the same environment and under the same conditions except nerves were not hooked or ligated.

Behavioural Assessment of the Neuropathic State

On post-operative days 2, 7, 9 and 14, behavioural signs of punctate mechanical and cooling hypersensitivity were assessed in the left ipsilateral hindpaw relative to the right contralateral hindpaw in awake and alert rats. Rats were individually placed in clear acrylic cubes on an elevated floor of wire mesh, and following a period of acclimation (30 minutes), mechanical sensitivities were determined by paw withdrawal to von Frey (vF) filaments with bending forces 2 g and 6 g (tested in consecutive, ascending force). Each filament was applied to the plantar surface of the paw for ~2-3 s with enough force to cause buckling, and for each animal this was repeated 10 times at set positions on each paw. The number of lifts in response to each of the filaments was noted for the contralateral and ipsilateral paw of each rat. Cold hypersensitivity was assessed by applying a drop of acetone to each paw 5 times during each testing period, with each application separated by an interval of at least 5 minutes. Withdrawal frequency was quantified as =(number of foot withdrawals/10 or 5 trials as appropriate).

The rotarod was also used to assess potential effects on motor performance of Netupitant and Palonosetron. Acceleration of the rotarod was set to increase from 0 to 20 revolutions per minute over the period of one minute. Due to initial, non-linear acceleration, rats were placed on the rotarod locked at a speed of 8 revolutions per minute. The rotarod was then set to accelerate and the latency to fall from the rotarod was timed from this point.

Electrophysiology

Electrophysiology experiments were conducted on post-operative days 14-17 in anaesthetised rats.

We recorded the evoked responses of dorsal horn lamina V-VI neurones to stimulation of the peripheral receptive field with:
- a train of 16 electrical pulses at 3×C-fibre threshold
- mechanical von Frey filaments of increasing force—vf 2 g, 8 g, 26 g and 60 g applied to the centre of the receptive field for 10 seconds
- heat—40, 45 and 48° C. applied to the centre of the receptive field by a constant water jet for 10 seconds Following 3 stable baseline responses, 0.03 mg/kg Palonosetron and 0.10 mg/kg Netupitant were administered into the scruff of the neck by subcutaneous injection. Drug effects were followed for two hours with tests carried out at 10, 30, 50, 70, 90 and 110 minutes post injection.

Explanation of Electrical Measurements

Input represents the post-synaptic C-fibre-evoked dorsal horn neuronal response following the first of the 16 electrical stimuli in the electrical train. It gives a measure of resting pre-synaptic activity (taken as total neuronal responsiveness upstream of the neurone under study, therefore including afferent excitability, activity at terminals and interneurones) and transmitter release in the absence of potentiation. The baseline 'input' response given numerically and graphically in this and other studies, was calculated as the number of C-fibre-evoked action potentials produced by the first stimulus (i.e. initial baseline response) multiplied by the total number of stimuli. Aβ-, Aδ-, and C-fibre responses denote the number of action potentials respectively generated in the spinal cord as a consequence of Aβ-, Aδ-, and C-fibre activity following electrical stimulation of their peripheral receptive field. Our Spike 2 Data Capturing software separates out which incoming action potentials are carried by which fibre according to their latency to arrive in the spinal cord following generation (given the different conduction velocities of the fibres). Thus, those arriving within 20 ms of peripheral stimulation are attributed to Aβ-fibres, Aδ-fibres=20-90 ms, and C-fibre-evoked responses were taken as those recorded 90-300 ms after electrical stimulation. Neuronal responses that trail behind between 300-800 ms post-stimulus are quantified as post-discharge, and represent spinal cord hyperexcitability that results as a consequence of repetitive stimulation of the neurone. Activity-dependent hyperexcitability can additionally be measured as wind-up. This value is calculated as the difference between the total number of action potentials at C-fibre latency produced by the train of 16 electrical stimuli, and 'input' as defined and calculated above. Therefore, if the first electrical stimulus elicited 15 C-fibre-evoked action potentials, and the total number of C-fibre-evoked action potentials recorded after 16 stimuli was 350, then wind up=350−(15×10)=200. If each post-synaptic response was independent of previous activity, then in the example above, the cumulative number of action potentials evoked by C-fibres after the 16 electrical stimuli should theoretically be 150. However, temporal summation of action potentials, and post-synaptic hyperexcitability amplify responses, so wind-up is a measure of the additional action potentials recorded above the predicted baseline level.

Statistical Analysis

Analyses were performed using GraphPad Prism version 4 for Apple Macintosh OS 10.4, (GraphPad Software, USA), and for all data a 95% confidence interval was used as a measure of statistical significance. Statistical significance with respect to behavioural scores was calculated using non-parametric Wilcoxon matched pairs tests. For electrophysiological data, statistical analyses were performed on raw data using two-way analysis of variance (ANOVA) for responses to mechanical and thermal stimuli, and if significant, Bonferroni post-hoc tests were performed. For responses to electrical stimulation and brush, student's t-tests were used to compare pre-drug baseline values with post-drug values. The data are expressed and presented as mean±SEM. Significance was taken as $P<0.05$*, $P<0.01$**

The data is reproduced in Tables 1-3 herein, and FIGS. 1-13.

TABLE 1

BEHAVIORAL ASSESSMENTS:
Paw Withdrawal Frequency (PWD) in SNL Rats

| Dose (mg/kg s.c.) | 2 g vF Filament | 6 g vF Filament | Cooling Acetone |
|---|---|---|---|
| Baseline | 5.0 ± 1.2 | 6.7 ± 1.1 | 2.9 ± 0.6 |
| 0.03 Palo | 2.8 ± 0.8 | 5.2 ± 1.5 | 1.2 ± 0.4 |
| 0.3 Palo | 3.1 ± 0.7 | 4.1 ± 1.3 | 1.2 ± 0.5 |
| 3 Palo | 1.4 ± 0.6 | 1.1 ± 0.4* | 1.9 ± 0.3 |
| Baseline | 4.4 ± 1.3 | 6.7 ± 1.2 | 2.8 ± 0.5 |
| 0.1 Netu | 4.1 ± 1.0 | 6.7 ± 1.8 | 1.9 ± 0.3 |
| 1 Netu | 3.8 ± 1.2 | 6.2 ± 1.5 | 2.7 ± 0.5 |
| 10 Netu | 3.9 ± 1.1 | 5.9 ± 1.0 | 2.0 ± 0.4 |
| Baseline | 4.1 ± 0.3 | 7.8 ± 0.5 | 3.6 ± 0.3 |
| 0.1 Netu + 0.03 Palo | 0.3 ± 0.1** | 1.8 ± 0.5** | 0.4 ± 0.2** |

Numbers as Mean ± S.E. (n = 7-9)

*p < 0.05

**p < 0.01 vs baseline

TABLE 2

ELECTROPHYSIOLOGICAL STUDIES:
Electrically-Evoked Dorsal Horn Neural Responses in SNL Rats - Number of Action Potentials

| Dose (mg/kg s.c.) | C-Fiber Response | AB-Fiber Response | AD-Fiber Response | Input Response | Post Discharge Response | Wind-up Response |
|---|---|---|---|---|---|---|
| Baseline | 408 ± 25 | 141 ± 9 | 137 ± 24 | 419 ± 70 | 299 ± 66 | 388 ± 93 |
| 0.03 Palo | 518 ± 103 | 141 ± 22 | 192 ± 51 | 461 ± 86 | 417 ± 127 | 559 ± 192 |
| Baseline | 403 ± 30 | 140 ± 7 | 142 ± 24 | 415 ± 65 | 225 ± 48 | 230 ± 56 |
| 0.1 mNetu | 292 ± 45 | 135 ± 10 | 103 ± 13 | 293 ± 46 | 195 ± 29 | 270 ± 38 |
| Baseline | 301 ± 43 | 116 ± 13 | 131 ± 17 | 244 ± 45 | 182 ± 31 | 273 ± 45 |
| 0.1 Netu + 0.03 Palo | 124 ± 29** | 104 ± 15 | 46 ± 13* | 54 ± 16** | 87 ± 37** | 145 ± 54 |

Numbers as Mean ± S.E. (n = 5-7)
*p < 0.05
**p < 0.01 vs baseline

TABLE 3

ELECTROPHYSIOLOGICAL STUDIES:
Electrically-Evoked Dorsal Horn Neural Responses in SNL Rats - Number of Action Potentials

| Dose (mg/kg s.c.) | Mechanically-Evoked | | | Heat-Evoked | | | Brush-Evoked |
|---|---|---|---|---|---|---|---|
| | 8 g vF Filament | 26 g vF Filament | 60 g vF Filament | 40° Celsius | 45° Celsius | 48° Celsius | |
| Baseline | 181 ± 53 | 564 ± 19 | 772 ± 101 | 311 ± 138 | 638 ± 195 | 915 ± 137 | 118 ± 43 |
| 0.03 Palo | 211 ± 42 | 539 ± 17 | 799 ± 192 | 136 ± 58 | 380 ± 187 | 816 ± 101 | 144 ± 59 |
| Baseline | 168 ± 51 | 385 ± 41 | 671 ± 105 | 473 ± 125 | 670 ± 159 | 971 ± 128 | 268 ± 35 |
| 0.1 Netu | 190 ± 42 | 390 ± 56 | 486 ± 75 | 298 ± 72 | 381 ± 82 | 495 ± 186 | 310 ± 40 |
| Baseline | 122 ± 54 | 368 ± 106 | 578 ± 106 | 189 ± 67 | 472 ± 97 | 659 ± 142 | 343 ± 78 |
| 0.1 Netu + 0.03 Palo | 30 ± 20 | 137 ± 41* | 242 ± 54** | 175 ± 42 | 186 ± 49** | 396 ± 122** | 199 ± 21 |

Numbers as Mean ± S.E. (n = 5-7)
*p < 0.05
**p < 0.01 vs baseline

Example 2

In a preferred embodiment the combination is administered in a capsule oral dosage form, wherein the capsule houses one or more soft-gel capsules for the palonosetron and one or more hard tablets for the netupitant. Table 4 below describes a representative formulation for a soft-gel capsule containing 0.5 mg. of palonosetron, suitable for inclusion in such a hard shell.

TABLE 4

REPRESENTATIVE SOFT-GEL FORMULATION

| Ingredient | Approximate Amount (mg./Capsule) | Function |
|---|---|---|
| Fill Solution | | |
| Palonosetron HCl | 0.56[1] | Active |
| Mono- and di-glycerides of Capryl/Capric Acid (Capmul MCM) | 62.19 | Solvent vehicle |
| Glycerin, anhydrous, USP/Ph Eur | 3.37 | Plasticizer |
| Polyglyceryl oleate (Plurol Oleique CC 497) | 0.87 | Surfactant |
| Purified water, USP/Ph Eur | 2.94 | Co-solvent |
| Butylated hydroxyanisole (BHA), NF/Ph Eur | 0.07 | Antioxidant |
| Nitrogen | — | |
| Theoretical fill weight | 70.00 mg. | |
| Gelatine Capsule Shell, 1.5-oval (Catalent Pharma Solutions)[2] | | |
| Gelatine (type 195), NF/Ph Eur | — | Shell |
| Sorbitol Special/Glycerin Blend 50/50 | — | Plasticizer |
| Titanium dioxide, USP/Ph Eur | — | Colorant/Opacifier |
| Purified water, USP/Ph Eur | — | Solvent |

[1]Corresponds to 0.50 mg. free base
[2]Quantitative composition of capsule shell is proprietary to Catalent Pharma Solutions Table 5 below describes a representative formulation for a tablet containing 100 mg. of netupitant, suitable for inclusion in a hard shell.

TABLE 5

REPRESENTATIVE TABLET FORMULATION

| Ingredient | Approximate Amount (mg./Tablet) | Function |
| --- | --- | --- |
| Netupitant, milled | 100 | Active |
| Microcrystalline cellulose pH 101 | 20.5 | Diluent and disintegrant |
| Sucrose Lauric Acid Esters | 10.0 | Surfactant |
| Polyvinilpyrrolidone K30 | 7.0 | Binder |
| Sodium croscaramellose | 3.0 | Disintegrant |
| Colloidal Silicon Dioxide | 3.0 | Glidant |
| Sodium Stearyl Fumarate | 1.0 | Lubricant |
| Magnesium Stearate | 0.5 | Lubricant |
| Total weight | 145 mg. | |

Example 3

Experiments were conducted to investigate the efficacy of Palonosetron (PT) and Netupitant (NT), individually and in combination, to inhibit acetic acid (AA)-induced colonic and somatic hypersensitivity in a rodent model. The overall goal was to determine if synergism would result when sub-therapeutic doses of both compounds were dosed in combination.

Materials and Methods

Animals: Male Sprague Dawley rats (330-480 g at time of colonic sensitivity assessment) were purchased from Charles River Laboratories. Rats were housed two-per-cage within the University of Oklahoma Health Sciences Center (OU-HSC) Department of Comparative Medicine's animal facility under controlled temperature and humidity. All animals had free access to food and water and were acclimated to facility housing for a minimum of one week before experimentation. A total of 85 rats were used to complete this study. The experimental protocol was approved by the University of Oklahoma Health Sciences Center (OUHSC) Institutional Animal Care and Use Committee (IACUC Animal Protocol #10-077).

Acclimation: Upon arrival all animals were acclimated to the animal facility for a minimum of one-week. To further acclimate and minimize experimental stress, the rats were brought to the laboratory for an additional week to acclimate to the laboratory environment and animal handlers.

Induction of Acute Visceral and Somatic Hypersensitivity: Visceral and somatic hypersensitivity were induced by infusing dilute (1.5 ml at 0.6%) acetic acid (AA) into the rat colon via a catheter (Intramedic PE 90 tubing) inserted via the anus to the level of the mid-colon. Within 60 mins colonic and somatic hypersensitivity was evident.

Colonic Sensitivity Assessment: Visceromotor responses (VMR) to colorectal distension (CRD) were measured by counting the number of abdominal contractions in response to increasing levels of CRD (0-60 mmHg). On the day of the colonic sensitivity assessment, a minor surgical procedure was performed to attach a strain gauge force transducer onto the abdominal oblique muscle and attached via an adapter cable to a Grass Model 7 Polygraph. The cable was connected to a Model 7P1 Low-Level DC Pre-Amp. The Pre-Amp was set at 0.02 mV/cm sensitivity and was connected to a Model 7DA DC Driver Amp with sensitivity set at 5.5 Amps. A 5 cm latex balloon was inserted into the distal colon. The balloon cannula was connected to a Distender Series IIR barostat (G & J Electronics Inc.) for controlled, isobaric inflation of the balloon and CRD using constant pressure (isobaric) tonic distensions were conducted at 0, 20, 40 and 60 mmHg. Each pressure was maintained for a period 10 min. during which time the number of abdominal muscle contractions were counted. A 10 min. recovery period was allowed between the each distension.

Somatic Sensitivity Assessment: Von Frey filaments were used to determine the level of somatic sensitivity in all animals receiving intracolonic infusion of AA. The Von Frey instrument measures the level of somatic sensitivity by recording the minimal force required to elicit hind paw withdrawal. The animals were placed in a mesh-bottomed Von Frey caging apparatus and a nylon filament was steadily pushed against the rat's foot pad until withdrawal of the hind paw. The force in grams which elicited hind paw withdrawal was then recorded.

Test Compounds: Following surgery, rats were pre-dosed with Palonosetron (1-hr pre-dose), Netupitant (2-hr pre-dose) or methyl cellulose vehicle. Palonosetron and Netupitant were supplied by Helsinn Healthcare Inc. and were stored at 4° C. until prepared for dosing as a suspension in 1% methyl cellulose solution. The drug suspensions were prepared so that each rat received an oral dosing volume of 0.5 ml per 100 g body weight for doses of 0.001, 0.01, 0.1 or 1 mg/kg. Compounds were prepared fresh on the day of use.

Statistical Analysis: To determine statistical significance between multiple control and treatment groups, data was compared using one-way ANOVA followed by a Bonferroni post-test. Results were deemed significant when p-values were less than 0.05.

Results

Effect of Palonosetron and Netupitant Combination on Somatic Hypersensitivity: As illustrated in FIG. 14, the oral administration of non-effective doses (0.001 mg/kg) of Palonosetron and Netupitant in combination resulted in a non-significant inhibitory trend toward normalization of somatic hypersensitivity.

The above experiments show that (1) infusion of dilute acetic acid into to the colon results in the development of both visceral and somatic hypersensitivity; (2) The 5-$HT_3$ antagonist Palonosetron significantly inhibited colonic and somatic hypersensitivity; (3) the $NK_1$ antagonist Netupitant significantly inhibited colonic sensitivity and somatic hypersensitivity; and (4) when non-effective doses (0.001 mg/kg) of Palonosetron and Netupitant were dosed in combination there was a significant inhibition of colonic sensitivity and a non-significant trend to inhibit somatic sensitivity. The above findings suggest that both Palonosetron and Netupitant could be further developed as possible therapeutic agents for the treatment of abdominal pain and GI dysfunction associated with IBS. Furthermore, the synergic effect shown in the non-effective combination dosing experiments, suggest that combination therapy using these two compounds may result in relief of IBS symptoms with less potential for unfavorable side-effects.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A synergistic drug combination comprising:
   a) palonosetron or a pharmaceutically acceptable salt or prodrug thereof; and
   b) netupitant or a pharmaceutically acceptable salt or prodrug thereof, in synergistically effective amounts.

2. The drug combination of claim 1, wherein said synergistically effective amounts when administered once daily to a 70 kg human are synergistically effective to treat mechanically evoked allodynia.

3. The drug combination of claim 1, wherein said synergistically effective amounts when administered once daily to a 70 kg human are synergistically effective to modulate electrically-evoked dorsal horn neural C-fiber responses.

4. The drug combination of claim 1, wherein said synergistically effective amounts when administered once daily to a 70 kg human are synergistically effective to modulate electrically-evoked dorsal horn neural AD-fiber responses.

5. The drug combination of claim 1, wherein said synergistically effective amounts when administered once daily to a human patient are synergistically effective to treat irritable bowel syndrome (IBS).

6. The drug combination of claim 1 in an orally administered dosage form, wherein said synergistically effective amounts comprise:
   a) from 0.01 to 1.0 mg of palonosetron or a pharmaceutically acceptable salt or prodrug thereof, based on the weight of the free base; and
   b) from 10 to 300 mg of netupitant or a pharmaceutically acceptable salt or prodrug thereof, based on the weight of the free base.

7. The drug combination of claim 1 in an orally administered dosage form, comprising:
   a) a sub-therapeutic dose of palonosetron or a pharmaceutically acceptable salt or prodrug thereof, wherein said sub-therapeutic dose is ineffective against irritable bowel syndrome when administered alone; and
   b) a sub-therapeutic dose of netupitant or a pharmaceutically acceptable salt or prodrug thereof, wherein said sub-therapeutic dose is ineffective against irritable bowel syndrome when administered alone.

8. The drug combination of claim 7 in an orally administered dosage form, comprising:
   a) palonosetron or a pharmaceutically acceptable salt thereof in a dose of less than 0.01 mg per kg body weight, based on the weight of the free base; and
   b) netupitant or a pharmaceutically acceptable salt thereof in a dose of less than 0.01 mg per kg body weight, based on the weight of the free base.

9. A method of treating chronic neuropathic pain comprising administering to a human patient in need thereof a drug combination comprising:
   a) palonosetron or a pharmaceutically acceptable salt or prodrug thereof; and
   b) netupitant or a pharmaceutically acceptable salt or prodrug thereof, in therapeutically effective amounts.

10. The method of claim 9, wherein said administration is oral, and said therapeutically effective amounts comprise on a daily basis:
    a) from 0.01 to 1.0 mg of palonosetron or a pharmaceutically acceptable salt or prodrug thereof, based on the weight of the free base; and
    b) from 10 to 300 mg of netupitant or a pharmaceutically acceptable salt or prodrug thereof, based on the weight of the free base.

11. The method of claim 9, wherein said neuropathic pain is caused by:
    a) systemic disease,
    b) trauma, or
    c) an infection or autoimmune disorder affecting nerve tissue.

12. The method of claim 9, wherein said neuropathic pain comprises diabetic peripheral neuropathic pain.

13. The method of claim 9, wherein said neuropathic pain comprises fibromyalgia.

14. The method of claim 9, wherein said neuropathic pain comprises post-herpetic neuralgia.

15. The method of claim 9 wherein said treatment, when administered to multiple humans, results in a statistically significant improvement in the number of patients having at least a 50% improvement in pain score from baseline, relative to placebo.

16. The method of claim 9 wherein said pain is unresponsive to one or more analgesic drugs selected from opioid analgesics, non-steroidal anti-inflammatory drugs (NSAIDs), tricyclic antidepressants (TCA) such as amitriptyline, and anticonvulsants such as gabapentin, phenyloin, and carbamazepine.

17. The method of claim 9 wherein said pain is accompanied by a comorbid diagnosis of major depressive disorder (MDD), anxiety and/or depression.

18. A method of treating irritable bowel syndrome (IBS) comprising administering to a human patient in need thereof,
    a) a therapeutically effective amount of palonosetron or a pharmaceutically acceptable salt or prodrug thereof; or
    b) a therapeutically effective amount of netupitant or a pharmaceutically acceptable salt or prodrug thereof; or
    c) a drug combination comprising:
       (i) a sub-therapeutic dose of palonosetron or a pharmaceutically acceptable salt or prodrug thereof, wherein said sub-therapeutic dose is ineffective against irritable bowel syndrome when administered alone; and
       (ii) a sub-therapeutic dose of netupitant or a pharmaceutically acceptable salt or prodrug thereof, wherein said sub-therapeutic dose is ineffective against irritable bowel syndrome when administered alone.

19. The method of claim 18, wherein said administration is oral, and said therapeutically effective amounts comprise on a daily basis:
    a) from 0.01 to 1.0 mg of palonosetron or a pharmaceutically acceptable salt or prodrug thereof, based on the weight of the free base; and
    b) from 10 to 300 mg of netupitant or a pharmaceutically acceptable salt or prodrug thereof, based on the weight of the free base.

20. The method of claim 18, wherein said administration is oral, and said sub-therapeutic dose comprises:
    a) palonosetron or a pharmaceutically acceptable salt thereof in a dose of less than 0.01 mg per kg body weight, based on the weight of the free base; and
    b) netupitant or a pharmaceutically acceptable salt thereof in a dose of less than 0.01 mg per kg body weight, based on the weight of the free base.

21. The method of claim 18, wherein said administration is oral, and said sub-therapeutic dose comprises:
    a) palonosetron or a pharmaceutically acceptable salt thereof in a dose of less than 0.001 mg per kg body weight, based on the weight of the free base; and
    b) netupitant or a pharmaceutically acceptable salt thereof in a dose of less than 0.001 mg per kg body weight, based on the weight of the free base.

22. The method of claim 18, wherein said IBS is selected from the group consisting of alternating IBS (IBS-A), IBS with diarrhea (IBS-D), and IBS with constipation (IBS-C).

23. The method of claim 18, wherein said method is non-gender specific.

24. The method of claim 18, wherein said IBS is IBS with constipation (IBS-C), and the method is effective to treat abdominal pain and constipation.

25. The method of claim 24, wherein said constipation is evaluated based on stool frequency.

26. The method of claim 25, wherein said method is effective to:
 a) decrease the intensity of said abdominal pain by 30 percent or more based on the weekly average of worst abdominal pain in previous 24 hours score as compared with baseline; and
 b) increasing complete spontaneous bowel movements (CSBM) per week at least once per week as compared with baseline.

27. The method of claim 18, wherein said IBS is IBS with diarrhea (IBS-D) and said method is effective to treat abdominal pain and diarrhea.

28. The method of claim 27, wherein said diarrhea is evaluated by accessing stool consistency.

29. The method of claim 28, wherein said stool consistency is described according to Bristol Stool Scale.

30. The method of claim 29, wherein said method is effective in:
 a) decreasing intensity of said abdominal pain by 30 percent or more based on weekly average of worst abdominal pain in previous 24 hours score as compared with baseline; and
 b) achieving a weekly average of equal to or less than type 5 of the Bristol Stool Chart.

31. The method of claim 24, wherein other symptoms of said IBS-C include abdominal discomfort.

32. The method of claim 27, wherein other symptoms of said IBS-D include abdominal discomfort and fecal incontinence.

33. The method of claim 18, wherein said IBS is caused by colonic and/or somatic hypersensitivity.

34. The method of claim 33, wherein said method is effective in inhibiting said colonic and/or somatic hypersensitivity.

* * * * *